(12) United States Patent
Hatsuda et al.

(10) Patent No.: US 6,586,549 B1
(45) Date of Patent: Jul. 1, 2003

(54) WATER-ABSORBING COMPOSITION AND ITS USE

(75) Inventors: Takumi Hatsuda, Takasago (JP); Kazuki Kimura, Himeji (JP); Koji Miyake, Okayama (JP); Eri Goto, Himeji (JP); Katsuyuki Wada, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 63 days.

(21) Appl. No.: 09/610,967

(22) Filed: Jul. 6, 2000

(30) Foreign Application Priority Data

Jul. 26, 1999 (JP) ............................................ 11-210222

(51) Int. Cl.⁷ ............................................. C08J 220/46
(52) U.S. Cl. .................... 526/317.1; 526/240; 526/295; 502/402; 528/484; 528/486; 524/437; 524/450
(58) Field of Search .................. 524/437, 450; 528/487, 486; 526/295, 317.1, 240; 502/402

(56) References Cited

U.S. PATENT DOCUMENTS

| | | | | |
|---|---|---|---|---|
| 4,734,478 A | * | 3/1988 | Tsubakimoto et al. ...... | 527/300 |
| 5,087,506 A | | 2/1992 | Palumbo ..................... | 428/194 |
| 5,147,343 A | | 9/1992 | Kellenberger ............... | 604/368 |
| 5,149,335 A | | 9/1992 | Kellenberger et al. ...... | 604/372 |
| 5,229,488 A | * | 7/1993 | Nagasuna et al. ........... | 524/430 |
| 5,382,610 A | | 1/1995 | Harada et al. .............. | 524/35 |
| 5,601,542 A | | 2/1997 | Melius et al. ............... | 604/368 |
| 5,668,078 A | | 9/1997 | Sumiya et al. .............. | 502/402 |
| 5,684,106 A | * | 11/1997 | Johnson et al. ............. | 526/295 |
| 5,720,736 A | * | 2/1998 | Hatsuda et al. ............. | 427/180 |
| 6,107,358 A | * | 8/2000 | Harada et al. .............. | 521/133 |
| 6,133,193 A | * | 10/2000 | Kajikawa et al. ........... | 428/402 |

FOREIGN PATENT DOCUMENTS

| | | |
|---|---|---|
| EP | 0493011 | 12/1991 |
| EP | 0532002 | 9/1992 |
| EP | 0629411 | 6/1994 |
| EP | 0761241 | 8/1996 |
| EP | 0 761241 | * 3/1997 |
| EP | 0837076 | 10/1997 |
| EP | 0 8444270 | * 5/1998 |
| EP | 0 874002 | * 10/1998 |
| EP | 0884037 | 12/1998 |
| JP | 531362 | 2/1993 |
| JP | 596159 | 4/1993 |
| JP | 788171 | 4/1995 |
| JP | 09124879 | 5/1997 |
| JP | 9124955 | 5/1997 |
| JP | 09136966 | 5/1997 |
| JP | 10265582 | 10/1998 |
| JP | 1158615 | 3/1999 |
| JP | 11267500 | 10/1999 |
| JP | 11286611 | 10/1999 |
| JP | 093792 | 4/2000 |
| WO | 9118042 | 11/1991 |
| WO | 9533558 | 12/1995 |

* cited by examiner

*Primary Examiner*—Tatyana Zalukaeva
(74) *Attorney, Agent, or Firm*—Roylance, Abrams, Berdo & Goodman, L.L.P.

(57) ABSTRACT

The present invention provides: a water-absorbing composition such that portions containing the water-absorbing composition in a high concentration exhibit excessive-liquid permeation buffering effects in absorbent articles comprising the water-absorbing composition and hydrophilic fibers; and a use of this water-absorbing composition. The water-absorbing composition comprises a water-absorbent resin and an excessive-liquid permeation buffer, wherein the water-absorbent resin is a product by a process including the step of further crosslinking the surface vicinity of a crosslinked polymer, and this water-absorbing composition is characterized by having a liquid permeation buffering index of not less than 0.4 and exhibiting an absorption capacity of not less than 25 g/g in absorbent structures under load, and further having an average particle diameter in the range of 200~600 μm, wherein the ratio of particles having particle diameters smaller than 106 μm in the water-absorbing composition is not more than 5 weight %. This water-absorbing composition is, for example, used for the absorbent articles comprising the water-absorbing composition and the hydrophilic fibers.

21 Claims, 3 Drawing Sheets

WATER-ABSORBING COMPOSITION AND ITS USE

BACKGROUND OF THE INVENTION

A. Technical Field

The present invention relates to a water-absorbing composition and its use.

B. Background Art

In recent years, water-absorbing agents such as water-absorbent resins are widely used as components of sanitary materials, such as disposable diapers, sanitary napkins and incontinent pads, for the purpose of causing the water-absorbing agents to absorb much water. In addition, the water-absorbing agents such as water-absorbent resins are widely used not only for the sanitary materials, but also for the purpose of absorbing or retaining water, like water-retaining agents for soil and drip sheets for foods.

Known examples of the above water-absorbing agents are as follows: partially-neutralized and crosslinked poly(acrylic acids); neutralized graft polymers of starch-acrylic acid; saponified copolymers of vinyl acetate-acrylic acid ester; hydrolyzed copolymers of acrylonitrile or acrylamide, or crosslinked polymers of these hydrolyzed copolymers; and crosslinked polymers of cationic monomers.

And, in order to use the above water-absorbing agents for the above sanitary materials and so on, the water-absorbing agents are desired to have properties (absorption properties) such as high absorption capacity or rate upon contact with aqueous liquids (e.g. body fluids) and high absorption capacity or liquid permeability under load. And various water-absorbing agents have been proposed so far, which jointly have various properties among the above absorption properties and exhibit excellent performances when used for the sanitary materials.

Furthermore, similarly to the water-absorbing agents, absorbent articles comprising the water-absorbing agents and hydrophilic fibers (e.g. pulp) are also desired to exhibit the following performances: a large absorption capacity when aqueous liquids (e.g. body fluids) are injected into absorbent structures; a large absorption capacity under load; and excellent diffusing ability for the aqueous liquids to spread over the whole absorbent structure.

The diffusing ability for the aqueous liquids (e.g. body fluids) to spread over the whole absorbent structure is related greatly to capillary phenomena of the hydrophilic fibers. That is to say, the concentration of the water-absorbing agent (hereinafter referred to as "resin concentration") in the absorbent article mainly comprising the water-absorbing agent and the hydrophilic fibers is conventionally in the range of about 20 to about 50 weight %, and the aqueous-liquid diffusing ability of the absorbent article comprising the water-absorbing agent in this range of weight ratio is dominated by diffusion due to capillary phenomena of the hydrophilic fibers.

Therefore, the absorbent structure in the above sanitary material has problems in that in the case where an aqueous liquid is injected in a large quantity at once into the absorbent structure, the aqueous liquid leaks out from edge portions of the absorbent article, because the water absorption rate of the water-absorbing agent is slower than the diffusion rate of the aqueous liquid in the absorbent structure.

SUMMARY OF THE INVENTION

A. Object of the Invention

An object of the present invention is to provide: a water-absorbing composition such that portions containing the water-absorbing composition in a high concentration exhibit excessive-liquid permeation buffering effects in absorbent articles comprising the water-absorbing composition and hydrophilic fibers; and a use of this water-absorbing composition.

B. Disclosure of the Invention

The present inventors made various studies to solve the above problems. As a result, they found that it is important to control the diffusion (to buffer the excessive permeation) of aqueous liquids when the water-absorbing composition comes into contact with the aqueous liquids in a state where the basis weight (resin concentration) of the water-absorbing composition is high and where particles of the water-absorbing composition closely cohere by external force. The above diffusion control (buffering of excessive permeation) of the aqueous liquids can be evaluated by introducing a new physical property value referred to as a liquid permeation buffering index. Then, the inventors completed the present invention by finding that the above problems can be solved by a water-absorbing composition which exhibits the following properties:

(1) The water-absorbing composition exhibits excellent water absorption properties in absorbent articles comprising the water-absorbing composition and hydrophilic fibers.

(2) The water-absorbing composition has a high liquid permeation buffering index, and can prevent the diffusion (buffer the excessive permeation) of aqueous liquids in the case where the resin concentration is high.

(3) If high resin concentration portions are placed on the periphery of the absorbent article as recited in (1) above, then the aqueous liquid can be prevented from leaking out from edge portions of the absorbent article when an aqueous liquid is injected in a large quantity at once into the absorbent article.

Accordingly, the present invention relates to a water-absorbing composition, which comprises a water-absorbent resin and an excessive-liquid permeation buffer, wherein the water-absorbent resin is a product by a process including the step of further crosslinking the surface vicinity of a crosslinked polymer, with the water-absorbing composition being characterized by having a liquid permeation buffering index of not less than 0.4 and exhibiting an absorption capacity of not less than 25 g/g in absorbent structures under load, and further having an average particle diameter in the range of 200~600 $\mu$m, wherein the ratio of particles having particle diameters smaller than 106 $\mu$m in the water-absorbing composition is not more than 5 weight %. The present invention further relates to an absorbent article, which comprises the above water-absorbing composition according to the present invention.

Incidentally, the above water-absorbing composition according to the present invention has an average particle diameter in the range of 200~600 $\mu$m, and the ratio of particles having particle diameters smaller than 106 $\mu$m in the water-absorbing composition is not more than 5 weight %.

These and other objects and the advantages of the present invention will be more fully apparent from the following detailed disclosure.

DETAILED DESCRIPTION OF THE INVENTION

Hereinafter, the present invention is explained in detail. The liquid permeation buffering index in the present invention is a new physical property value for evaluating the prevention of the diffusion of aqueous liquids (excessive-liquid permeation buffering effects) when the water-absorbing composition comes into contact with the aqueous liquids in a state where the basis weight (resin concentration) of the water-absorbing composition is high and where particles of the water-absorbing composition closely cohere by external force.

Incidentally, in the present invention, the liquid permeation buffering index of the water-absorbing composition, the absorption capacity of the water-absorbing composition in absorbent structures under load, the absorption capacity of the water-absorbing composition or water-absorbent resin without load, the absorption capacity of the water-absorbent resin under load, and the average particle diameter were measured in the following ways.

(a) Liquid Permeation Buffering Index:

Hereinafter, first, the measurement apparatus as used for measuring the liquid permeation buffering index is simply explained while referring to FIG. 1.

Figure 1:
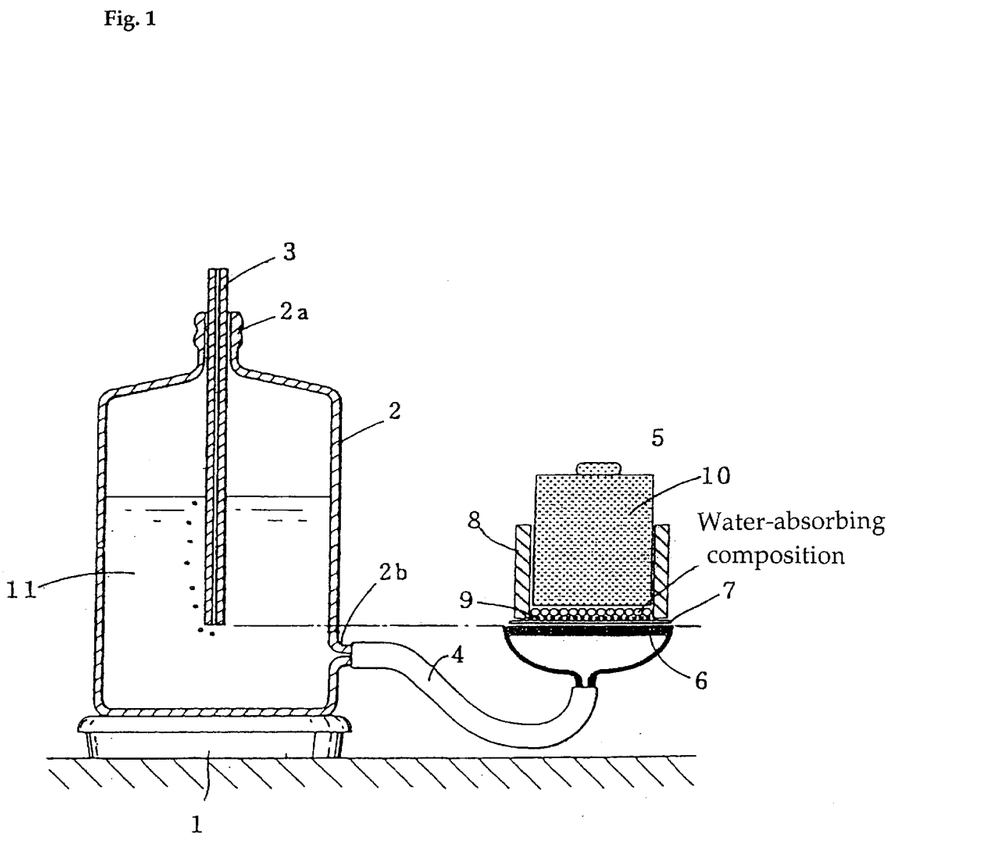
FIG. 1 is a schematic section of a measurement apparatus as used for measuring the liquid permeation buffering index, which represents one of performances of the water-absorbing composition according to the present invention, and further measuring the absorption capacity of the water-absorbent resin under load.

As is shown in FIG. 1, the measurement apparatus comprises: a balance 1; a container 2 of a predetermined capacity as mounted on the balance 1; an air-intake pipe 3; a conduit 4; a glass filter 6; and a measurement section 5 as mounted on the glass filter 6.

The container 2 has an opening 2a on the top and an opening 2b on the side. The air-intake pipe 3 is inserted through the opening 2a, and the conduit 4 is fitted to the opening 2b. Incidentally, the container 2 is filled with a predetermined amount of 0.9 weight % aqueous sodium chloride solution (hereinafter referred to as physiological saline solution) 11.

In addition, the lower end part of the air-intake pipe 3 is submerged in the physiological saline solution 11. The air-intake pipe 3 is set to keep the internal pressure of the container 2 substantially constant (atmospheric pressure).

The glass filter 6 is formed in a diameter of 70 mm. The container 2 and the glass filter 6 are connected to each other through the conduit 4 made of silicone resin. In addition, the position and level of the glass filter 6 are fixed relative to the container 2. Furthermore, the upper face of the glass filter 6 is fixed so as to be located a little higher than the lower end of the air-intake pipe 3.

The measurement section 5 comprises: paper filter 7; a supporting cylinder 8; a metal gauze 9 as attached to the bottom of the supporting cylinder 8; and a weight 10. The measurement section 5 is formed by mounting the paper filter 7 and the supporting cylinder 8 (i.e. metal gauze 9) in this order on the glass filter 6 and further mounting the weight 10 inside the supporting cylinder 8, namely, on the metal gauze 9. The supporting cylinder 8 is formed in an inner diameter of 60 mm. The metal gauze 9 is made of stainless steel and formed in 400 mesh (mesh opening size: 38 μm). An arrangement is made such that a predetermined amount of water-absorbing composition can uniformly be spread onto the metal gauze 9. In addition, the weight 10 is adjusted in weight such that a load of 20 g/cm$^2$ (=about 1.9 kPa) can uniformly be applied to the metal gauze 9, namely, to the water-absorbing composition.

The liquid permeation buffering index was measured with the measurement apparatus having the above constitution. The measurement method is hereinafter explained.

First, predetermined preparatory operations were made, in which, for example, a predetermined amount of physiological saline solution 11 was placed into the container 2, and the air-intake pipe 3 was inserted into the container 2. Next, the paper filter 7 was mounted on the glass filter 6. On the other hand, in parallel with this mounting operation, 0.9 g of water-absorbing composition was uniformly spread into the supporting cylinder 8, namely, onto the metal gauze 9, and the weight 10 was put on this water-absorbing composition.

Next, the metal gauze 9, namely, the supporting cylinder 8 (in which the water-absorbing composition and the weight 10 were put), was mounted on the paper filter 7 such that the center line of the supporting cylinder 8 would conform with that of the glass filter 6.

Then, the weight $W_1$ (g) of the physiological saline solution 11, as absorbed by the water-absorbing composition over a period of 60 minutes since the supporting cylinder 8 had been mounted on the paper filter 7, was determined from a value as measured with the balance 1.

Then, the liquid permeation buffering index, as of 60 minutes after the initiation of the water absorption, was calculated from the above weight $W_1$ (g) and the weight of the water-absorbing composition (0.9 g) in accordance with the following equation:

Liquid permeation buffering index=10/{(weight $W_1$ (g))/(weight (g) of water-absorbing composition)}

Incidentally, the liquid permeation buffering index as determined by the above operations indicates the extent of the excessive-liquid permeation buffering effects in the case where the water-absorbing composition according to the present invention is used in high resin concentration in absorbent articles.

(b) Absorption Capacity of Water-absorbing Composition in Absorbent Structures Under Load:

Hereinafter, first, the measurement apparatus as used for measuring the absorption capacity of the water-absorbing composition in absorbent structures under load is explained while referring to FIG. 2. Incidentally, for convenience' sake of the explanation, the same symbols as those of the aforementioned measurement apparatus for measuring the liquid permeation buffering index are used, and the explanation of such symbols is omitted.

Figure 2:
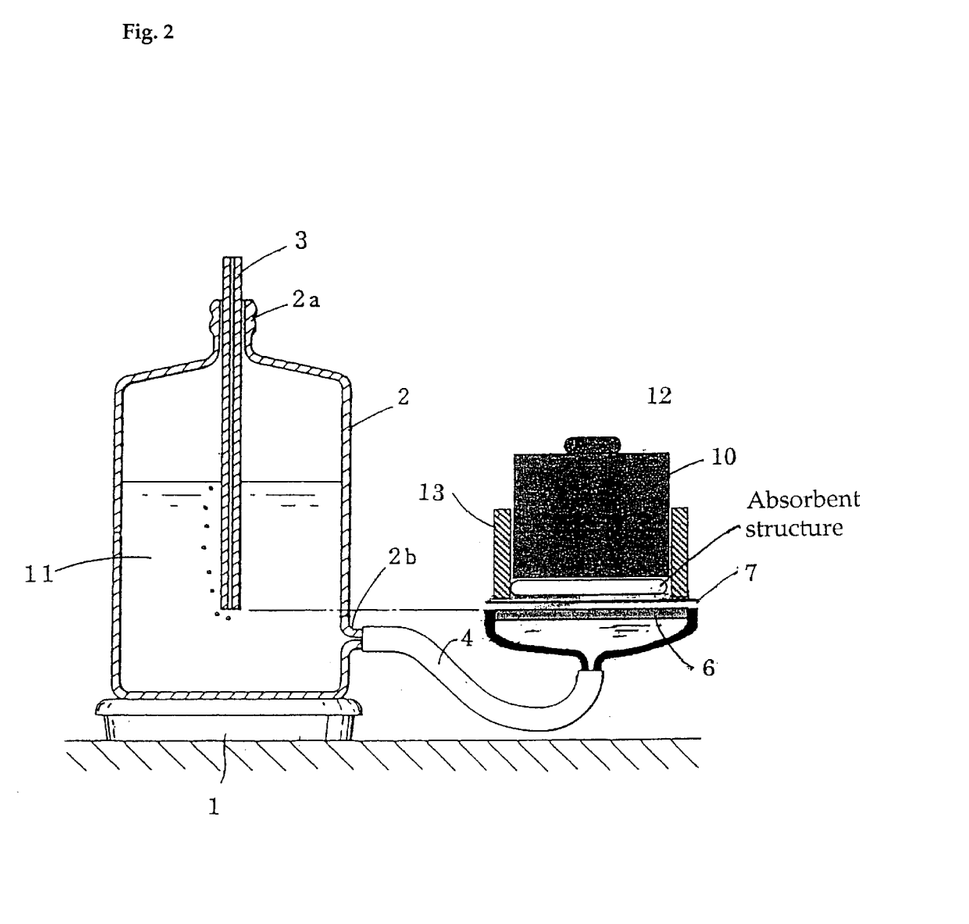
FIG. 2 is a schematic section of a measurement apparatus as used for measuring the absorption capacity of the water-absorbing composition in absorbent structures under load which represents one of performances of the water-absorbing composition according to the present invention.

As is shown in FIG. 2, the measurement apparatus comprises: a balance 1; a container 2; an air-intake pipe 3; a conduit 4; a glass filter 6 as formed in a diameter of 140 mm; and a measurement section 12 as mounted on the glass filter 6. The measurement section 12 comprises paper filter 7, a supporting square cylinder 13, and a weight 10. Incidentally, the measurement section 12 does not have the aforementioned metal gauze.

The measurement section 12 is formed by mounting the paper filter 7 and the supporting square cylinder 13 in this order on the glass filter 6 and further mounting the weight 10 inside the supporting square cylinder 13. The supporting square cylinder 13 is formed in inner measurements of 100 mm×100 mm. And an arrangement is made such that an absorbent structure of the predetermined size can be put in the supporting square cylinder 13, and further that the weight 10 can apply a load of 20 g/cm$^2$ (=about 1.9 kPa) uniformly to the absorbent structure. The other constitution of the measurement apparatus is the same as that of the aforementioned measurement apparatus for measuring the liquid permeation buffering index.

The absorption capacity of the water-absorbing composition in absorbent structures under load was measured with the measurement apparatus having the above constitution. The measurement method is hereinafter explained. Incidentally, the absorbent structure to be measured was produced in the following way. First, 50 weight parts of water-absorbing composition and 50 weight parts of wood-pulverized pulp (as hydrophilic fibers), which was usually used for sanitary materials such as disposable diapers, were mixed together in a dry manner with a mixer. Next, the resultant mixture was shaped into a web of the size of 100 mm×100 mm, and then this web was pressed under a pressure of 2 kg/cm$^2$ (=about 196 kPa) for 1 minute, thus obtaining an absorbent structure having a basis weight of 0.047 g/cm$^2$.

Furthermore, to measure the absorption capacity of the hydrophilic fibers alone in the absorbent structure under load, a blank absorbent structure was produced in the following way. First, wood-pulverized pulp (as hydrophilic fibers) was shaped into a web of the size of 100 mm×100 mm, and then this web was pressed under a pressure of 2 kg/cm$^2$ (=about 196 kPa) for 1 minute, thus obtaining an absorbent structure having a basis weight of 0.0235 g/cm$^2$.

First, the predetermined preparatory operations for the measurement apparatus were made. Next, the paper filter 7 was mounted on the glass filter 6. Then, the supporting square cylinder 13 was mounted on the paper filter 7 such that the center line of the supporting square cylinder 13 would conform with that of the glass filter 6.

Thereafter, the absorbent structure was mounted in the supporting square cylinder 13, namely, on the paper filter 7, and then the weight 10 was mounted on this absorbent structure. Incidentally, the operations of mounting the absorbent structure and the weight 10 were quickly made.

Then, the weight of the physiological saline solution 11, as absorbed by the absorbent structure over a period of 60 minutes since the absorbent structure had been mounted on the paper filter 7, was measured with the balance 1. Incidentally, the weight of the physiological saline solution 11, as absorbed by the absorbent structure which was a mixture of the water-absorbing composition and the hydrophilic fibers, was denoted by $W_2$ (g); and the weight of the physiological saline solution 11, as absorbed by the blank absorbent structure of the hydrophilic fibers alone, was denoted by $W_3$ (g).

Then, the absorption capacity (g/g) of the water-absorbing composition in absorbent structures under load, as of 60 minutes after the initiation of the absorption, was calculated from the above weights $W_2$ and $W_3$ in accordance with the following equation:

Absorption capacity (g/g) of water-absorbing composition in absorbent structures under load=(weight $W_2$ (g)−weight $W_3$ (g))/(weight (g) of water-absorbing composition)

Incidentally, the absorption capacity of the water-absorbing composition in absorbent structures under load, as determined by the above operations, indicates the extent of the actual absorption capacity in the case where the water-absorbing composition according to the present invention is used in absorbent articles.

(c) Absorption Capacity Without Load:

First, 0.2 g (=weight $W_0$ g) of water-absorbing composition (or water-absorbent resin) was uniformly placed into a nonwoven-fabric-made bag (60 mm×60 mm) and then immersed into physiological saline solution at room temperature. Thirty minutes later, the bag was drawn up and then drained at 250 G (250×9.81 m/s$^2$) for 3 minutes with a centrifuge, and the weight $W_4$ (g) of the bag was then measured. On the other hand, the same procedure was carried out using no water-absorbing composition (or no water-absorbent resin), and the resultant weight $W_5$ (g) was measured. Thus, the absorption capacity (g/g) without load was calculated from the above weights $W_0$, $W_4$ and $W_5$ in accordance with the following equation:

Absorption capacity (g/g) without load=(weight $W_4$ (g)−weight $W_5$ (g))/(weight $W_0$ (g))

(d) Absorption Capacity of Water-absorbent Resin Under Load:

The weight $W_6$ (g) of physiological saline solution 11, as absorbed by the water-absorbent resin over a period of 60 minutes, was determined from a value as measured with the balance 1 by the same method as the aforementioned one used for measuring the liquid permeation buffering index, except that the water-absorbent resin was substituted for the water-absorbing composition.

Then, the absorption capacity of the water-absorbent resin under load, as of 60 minutes after the initiation of the water absorption, was calculated from the above weight $W_6$ (g) and the weight of the water-absorbent resin (0.9 g) in accordance with the following equation:

Absorption capacity (g/g) of water-absorbent resin under load= (weight $W_6$ (g))/(weight (g) of water-absorbent resin)

(e) Average Particle Diameter:

The particle diameter distribution of the water-absorbing composition, the water-absorbent resin, and the water-absorbent resin precursor was measured with JIS standard screens comprising mesh opening sizes of 850 μm, 600 μm, 500 μm, 425 μm, 300 μm, 150 μm, and 106 μm respectively and receivers. Then, the average particle diameter $D_{50}$ was determined from the measured particle diameter distribution and the values of the mesh opening sizes with a logarithmic normal distribution graph.

In addition, in the case where the particles had a narrow uniform particle diameter distribution (such as classified into 500~425 μm) and where a plurality of JIS standard screens were not present between upper and lower limits of the particle diameter distribution, the average of these upper and lower limits (in the above example, 463 μm) was taken as the average particle diameter.

The means for obtaining the water-absorbing composition according to the present invention is not especially limited, but can fitly be set according to uses. Specifically, the water-absorbing composition is a obtained by a process including the steps of: polymerizing a hydrophilic unsaturated monomer to obtain a crosslinked polymer; further crosslinking the surface vicinity of the resultant crosslinked polymer to obtain a water-absorbent resin; and then mixing the resultant water-absorbent resin with an excessive-liquid permeation buffer. The crosslinked polymer herein referred to is a water-absorbent resin precursor.

Preferable examples of the water-absorbent resin, which is a component of the water-absorbing composition according to the present invention, include a hydrophilic crosslinked polymer containing a carboxyl group. This hydrophilic crosslinked polymer is, for example, a product by a process including the step of (co)polymerizing (hereinafter referred to simply as polymerizing) a hydrophilic unsaturated monomer including a major proportion of acrylic acid and/or its salt. Crosslinked polymers of polyacrylate salts are more preferable among the hydrophilic crosslinked polymers. In addition, preferably, 50~90 mol % of the acid groups of the crosslinked polymer are in the form of neutralized salts such as alkaline metal salts, ammonium salts, and amine salts. This neutralization of the acid group may be carried out in a manner such that the hydrophilic unsaturated monomer is neutralized in its preparation step before the initiation of the polymerization reaction to obtain the crosslinked polymer, or that the acid group of the resultant crosslinked polymer is neutralized in the course of the polymerization reaction or after its end.

The above hydrophilic unsaturated monomer may further comprise unsaturated monomers other than the above acrylic acid and its salt (hereinafter referred to as other monomers), if necessary. Specific examples of the above other monomers include: anionic unsaturated monomers and their salts, such as methacrylic acid, maleic acid, vinylsulfonic acid, styrenes- ulfonic acid, 2-(meth)acrylamido-2-methylpropanesulfonic acid, 2-(meth)acryl- oylethane-sulfonic acid, and 2-(meth)acryloylpropanesulfonic acid; nonionic unsaturated monomers including a hydrophilic group, such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl(meth)acrylate, 2-hydroxypropyl(meth)acrylate, methoxypolyethylene glycol(meth)acrylate, polyethylene glycol mono(meth)acrylate, vinylpyridine, N-vinylpyrrolidone, N-acryloylpiperidine, and N-acryloylpyrrolidine; cationic unsaturated monomers such as N,N-dimethylaminoethyl(meth)acrylate, N,N-diethylaminoethyl (meth)acrylate, N,N-dimethylaminopropyl(meth)acrylate, N,N-dimethylaminopropyl(meth)acrylamide, and their quaternary salts. However, there is no especial limitation thereto. When these other monomers are also used, the amount thereof is preferably not larger than 30 mol %, more preferably not larger than 10 mol %, of the total of the hydrophilic unsaturated monomer.

The water-absorbent resin precursor, which is a product by a process including the step of polymerizing the hydrophilic unsaturated monomer, has a carboxyl group. When the water-absorbent resin precursor is produced, it is desirable to introduce a crosslinking structure into internal portions using an internal-crosslinking agent. This internal-crosslinking agent is not especially limited if it is a compound which has at least two reactive groups, reactable with a polymerizable unsaturated group and/or a carboxyl group, per molecule, in other words, a compound which has at least two substituents, copolymerizable and/or reactable with the hydrophilic unsaturated monomer, per molecule. Incidentally, the hydrophilic unsaturated monomer may comprise a self-crosslinking type compound which is formable into a crosslinking structure even if no internal-crosslinking agent is used.

Specific examples of the internal-crosslinking agent include: N,N'-methylenebis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerol tri(meth)acrylate, glycerol acrylate methacrylate, ethylene-oxide-denatured trimethylolpropane tri(meth)acrylate, pentaerythritol tetra(meth)acrylate, dipentaerythritol hexa (meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, polyethylenimine, and glycidyl(meth)acrylate. However, there is no especial limitation thereto. These internal-crosslinking agents may be used either alone respectively or in combinations with each other. Among the above-exemplified internal-crosslinking agents, the use of those which have at least two polymerizable unsaturated groups per molecule can further improve such as absorption properties of the resultant water-absorbing composition.

The amount of the internal-crosslinking agent as used is preferably in the range of 0.005~3 mol %, more preferably 0.01~1.5 mol %, of the hydrophilic unsaturated monomer. Both in the case where the amount of the internal-crosslinking agent is smaller than 0.005 mol % and in the case where the amount of the internal-crosslinking agent exceeds 3 mol %, the water-absorbing composition having desirable water absorption properties might not be obtained.

Incidentally, when the water-absorbent resin precursor is produced by the process including the step of polymerizing the hydrophilic unsaturated monomer, hydrophilic polymers may be graft-polymerized, and further, chain transfer agents, such as hypophosphorous acid (and its salts), and water-soluble or water-dispersible surfactants may be added into the reaction solution.

The method for polymerizing the hydrophilic unsaturated monomer is not especially limited, but conventional methods such as aqueous solution polymerization, reversed-phase suspension polymerization, bulk polymerization and precipitation polymerization can be employed. Particularly, methods in which the hydrophilic unsaturated monomer is polymerized in their aqueous solution, namely, aqueous solution polymerization and reversed-phase suspension polymerization, are preferable for the easiness of the control of the polymerization reaction and for the performance of the resultant water-absorbing composition.

The concentration of the aqueous solution of the monomer components in the above polymerization method, in other words, the ratio of the monomer components in their aqueous solution, is not especially limited, but is preferably not lower than 10 weight %, more preferably in the range of 10~50 weight %, still more preferably in the range of 15~40 weight %. In addition, the reaction conditions such as reaction temperature and reaction time may fitly be set according to factors such as composition of the monomer components as used, and are therefore not especially limited.

In addition, the polymerization of the hydrophilic unsaturated monomer may involve the use, for example, of: radical polymerization initiators, such as potassium persulfate, sodium persulfate, ammonium persulfate, t-butyl hydroperoxide, hydrogen peroxide, and 2,2'-azobis(2-amidinopropane)dihydrochloride; radical photopolymerization initiators, such as 2-hydroxy-2-methyl-1-phenylpropan-1-one; or active energy rays, such as ultraviolet rays and electron beam. In addition, when oxidizing radical polymerization initiators are used, redox polymerization may be carried out using reducing agents, such as sodium sulfite, sodium hydrogensulfite, ferrous sulfate, and L-ascorbic acid, jointly with the oxidizing radical polymerization initiators. The amount of the above polymerization initiator, as used, is in the range of preferably 0.001~2 mol %, more preferably 0.01~0.5 mol %.

As to the water-absorbent resin precursor obtained by the above polymerization method, its particle diameter is arranged by operations such as drying, pulverization, and classification, if necessary. The water-absorbent resin precursor may have various shapes such as spherical shape, scaly shape, irregular pulverized shape, fibrous shape, granular shape, bar shape, approximately spherical shape, and flat shape.

The process for producing the water-absorbent resin precursor preferably includes the step of arranging the particle diameter of the water-absorbent resin precursor by repeating operations such as pulverization and classification such that the average particle diameter can fall into the range of 200~600 µm, and that the ratio of particles having particle diameters smaller than 106 µm can fall into the range of not more than 5 weight %, more preferably not more than 3 weight %, still more preferably not more than 1 weight %. In the case where the average particle diameter of the water-absorbent resin precursor is larger than 600 µm, there are disadvantages in that the ratio of coarse particles in the resultant water-absorbing composition is so high that the coarse particles give users an uncomfortable feeling when the water-absorbing composition is practically used for absorbent articles. In addition, in the case where the average particle diameter of the water-absorbent resin precursor is smaller than 200 µm, there are disadvantages in that such a small average particle diameter involves the increase of the ratio of particles having particle diameters smaller than 106 µm. In addition, in the case where the ratio of particles having particle diameters smaller than 106 µm in the water-absorbent resin precursor is more than 5 weight %, openings in absorbent structures are clogged with fines particles, therefore it might be difficult to obtain the water-absorbing composition which exhibits a high absorption capacity in absorbent structures under load. Particularly, in the case where the ratio of particles having particle diameters smaller than 106 µm is more than 5 weight %, powder dust occurs, so there are disadvantages in respect to working environment.

The water-absorbent resin, which is used in the present invention and is a product by a process including the step of further crosslinking the surface vicinity of the water-absorbent resin precursor, is obtainable by a process including the step of treating particles of the above water-absorbent resin precursor in the presence of a surface-crosslinking agent, thereby surface-crosslinking the particles of the water-absorbent resin precursor. Examples of the surface-crosslinking method include a method comprising the step of heating the water-absorbent resin precursor with either one of the below-mentioned first and second surface-crosslinking agents, or in the presence of a surface-crosslinking agent which comprises a combination of the first and second surface-crosslinking agents. Particularly, it is preferable that the surface-crosslinking treatment is carried out in the presence of the surface-crosslinking agent which comprises the combination of the first and second surface-crosslinking agents. The above surface-crosslinking can increase the crosslinking density of the surface vicinity of the water-absorbent resin particles to a higher one than the crosslinking density of internal portions of the water-absorbent resin particles, and therefore can give a water-absorbing composition which exhibits a high absorption capacity in absorbent structures under load.

The surface-crosslinking agent is a compound reactable with the carboxyl group of the water-absorbent resin precursor, and preferably comprises a combination of a first surface-crosslinking agent and a second surface-crosslinking agent whose solubility parameters (SP values) are deferent from each other. Incidentally, the above solubility parameter is a value as commonly used as a factor indicating the polarity of compounds. The values of solubility parameters, $\sigma$ $(cal/cm^3)^{1/2}$, of solvents, as disclosed on pages 527~539 of *Polymer Handbook*, 3rd edition (published by WILEY INTERSCIENCE), are applied to the above solubility parameter in the present invention. In addition, values, as applied to solubility parameters of solvents as not disclosed on the above pages, are led by substituting Hoy's cohesive energy constant, as disclosed on page 525 of the *Polymer Handbook* above, for Small's equation as disclosed on page 524 of the *Polymer Handbook* above.

The above first surface-crosslinking agent is preferably a compound which is reactable with the carboxyl group of the water-absorbent resin precursor and has a solubility parameters of not less than 12.5 $(cal/cm^3)^{1/2}(25.6 \times 10^3$ $(J/m^3)^{1/2})$, more preferably not less than 13.0 $(cal/cm^3)^{1/2}(26.6 \times 10^3$ $(J/m^3)^{1/2})$. Specific examples of the first surface-crosslinking agent include ethylene glycol, propylene glycol, glycerol, pentaerythritol, sorbitol, ethylene carbonate (1,3-dioxolan-2-one), and propylene carbonate (4-methyl-1,3-dioxolan-2-one), but the first surface-crosslinking agent is not limited to these compounds. These first surface-crosslinking agents may be used either alone respectively or in combinations with each other.

The above second surface-crosslinking agent is preferably a compound which is reactable with the carboxyl group of the water-absorbent resin precursor and has a solubility parameter less than 12.5 $(cal/cm^3)^{1/2}(25.6 \times 10^3$ $(J/m^3)^{1/2})$, more preferably in the range of 9.5 to 12.0 $(cal/cm^3)^{1/2}$ $(19.4 \times 10^3$ to $24.6 \times 10^3$ $(J/m^3)^{1/2})$. Specific examples of the second surface-crosslinking agent include diethylene glycol, triethylene glycol, tetraethylene glycol, dipropylene glycol, tripropylene glycol, 1,3-butanediol, 1,4-butanediol, 1,5-pentanediol, 2,4-pentanediol, 1,6-hexanediol, 2,5-hexanediol, trimethylolpropane, diethanolamine, triethanolamine, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, ethylenediamine, diethylenetriamine, triethylenetetramine, 2,4-tolylene diisocyanate, 4,5-dimethyl-1,3-dioxolan-2-one, epichlorohydrin, and epibromohydrin, but the second surface-crosslinking agent is not limited to these compounds. These second surface-crosslinking agents may be used either alone respectively or in combinations with each other.

The amount of the surface-crosslinking agent as used depends on the compounds as used as the surface-crosslinking agent, or on combinations thereof, but is preferably in the range of 0.01 to 5 weight parts of the first surface-crosslinking agent and 0.001 to 1 weight part of the second surface-crosslinking agent, and more preferably in the range of 0.1 to 2 weight parts of the first surface-crosslinking agent and 0.005 to 0.5 weight parts of the second surface-crosslinking agent, per 100 weight parts of the solid content of the water-absorbent resin precursor. The use of the surface-crosslinking agent in an amount larger than the above ranges is unfavorable, because such an amount is not only uneconomical, but also excessive to the formation of the optimal crosslinking structure in the water-absorbent resin. In addition, in the case where the amount of the surface-crosslinking agent as used is smaller than the above ranges, it might be difficult to obtain the water-absorbing composition which exhibits a high absorption capacity in absorbent structures under load.

When the water-absorbent resin precursor and the surface-crosslinking agent are mixed together, water is preferably used as a solvent. The amount of water as used depends upon such as type or particle diameter of the water-absorbent resin precursor, but is preferably in the range of 0 to 20 weight parts (but not including 0 weight parts), more preferably in the range of 0.5 to 10 weight parts, per 100 weight parts of the solid content of the water-absorbent resin precursor.

In addition, when the water-absorbent resin precursor and the surface-crosslinking agent are mixed together, a hydrophilic organic solvent may be used as a solvent, if necessary. Specific examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and alkoxypolyethylene glycols; amides such as N,N-dimethylformamide; and sulfoxides such as dimethyl sulfoxide. The amount of the hydrophilic organic solvent as used depends upon such as type or particle diameter of the water-absorbent resin precursor, but is preferably not larger than 20 weight parts, more preferably in the range of 0.1 to 10 weight parts, per 100 weight parts of the solid content of the water-absorbent resin precursor.

In addition, examples of methods for mixing the water-absorbent resin precursor and the surface-crosslinking agent together include a method comprising the steps of dispersing the water-absorbent resin precursor into the above-exemplified hydrophilic organic solvent, and then mixing the resultant dispersion with the surface-crosslinking agent. However, the mixing method is not especially limited. Preferable among various mixing methods is a method comprising the step of spraying or dropping the surface-crosslinking agent (as dissolved in either one or both of water and the hydrophilic organic solvent, if necessary) directly onto the water-absorbent resin precursor, thus mixing them.

A mixing apparatus as used to mix the water-absorbent resin precursor and the surface-crosslinking agent together (this mixing apparatus is hereinafter referred to as "mixing apparatus a") is desired to have great mixing power to homogeneously and surely mix them. Preferable examples of this "mixing apparatus a" include cylinder type mixers, double-wall cone type mixers, V-character-shaped mixers, ribbon type mixers, screw type mixers, fluidized-furnace rotary disk type mixers, gas current type mixers, twin-arm kneaders, internal mixers, pulverizing type kneaders, rotary mixers, screw type extruders, and turbilizers.

After mixing the water-absorbent resin precursor and the surface-crosslinking agent together, a thermal treatment is carried out to crosslink the surface vicinity of the water-absorbent resin precursor, thus obtaining a water-absorbent resin. The treatment temperature in this thermal treatment depends upon the surface-crosslinking agent as used, but is preferably in the range of 80 to 250° C. as the temperature of the materials or heating medium. In the case where the treatment temperature is lower than 80° C., there are disadvantages in that no uniform crosslinking structure is formed and it is therefore impossible to obtain the water-absorbing composition which exhibits a high absorption capacity in absorbent structures under load, and further in that a long time is needed for the thermal treatment, therefore the productivity is lowered. In the case where the treatment temperature is higher than 250° C., there are disadvantages in that the water-absorbent resin precursor is degraded, therefore the performance of the water-absorbing composition is deteriorated.

The above thermal treatment can be carried out with conventional driers or heating furnaces. Examples of the driers include channel type mixing driers, rotary driers, disk driers, fluidized-bed driers, gas current type driers, and infrared driers.

The excessive-liquid permeation buffer, which is a component of the water-absorbing composition according to the present invention, is not especially limited if it is such that when the water-absorbing composition comes into contact with aqueous liquids, for example, particles of the water-absorbing composition can closely cohere to prevent the aqueous liquids from flowing between the particles (exhibit excessive-liquid permeation buffering effects). However, the excessive-liquid permeation buffer is preferably in the form of fine particles such that the viscosity of a 1 weight % aqueous solution of the excessive-liquid permeation buffer as measured under conditions of 25° C., pH=7, and 25 rpm with a Brookfield rotating viscometer (hereinafter referred to as 1 weight % aqueous solution viscosity) (as to an excessive-liquid permeation buffer which is not soluble in water, the viscosity is measured in a state where the excessive-liquid permeation buffer is dispersed in water) is not lower than 1 Pa·s, more preferably not lower than 5 Pa·s, still more preferably not lower than 10 Pa·s. Fine particles which exhibits a 1 weight % aqueous solution viscosity lower than 1 Pa·s have disadvantages in that a large amount of excessive-liquid permeation buffer needs to be added and therefore deteriorates the uniform mixability when mixed with the water-absorbent resin. Specific examples of the excessive-liquid permeation buffer which is finely particulate include organic fine particles such as cellulose derivatives (e.g. carboxymethyl cellulose, hydroxyethyl cellulose, and hydroxypropyl cellulose), starch, starch derivatives, poly(ethylene oxides), poly(vinylpyrrolidones), poly(acrylic acids) (and their salts), and crosslinked poly(acrylic acids) (and their salts). Among them, the poly(acrylic acids) are preferable, and the crosslinked poly(acrylic acids) are more preferable for enhancing the gel stability. In addition, the above-exemplified excessive-liquid permeation buffers may be used either alone respectively or in combinations with each other.

In addition, in the case where inorganic fine particles which exhibit a 1 weight % aqueous solution viscosity lower than 1 Pa·s, such as bentonite, silicon dioxide, titanium oxide, and aluminum oxide, are used as the excessive-liquid permeation buffer, although the cause is not clear, if the gel strength is weakened by enhancing the absorption capacity of the water-absorbent resin without load before the water-absorbent resin is mixed with the excessive-liquid permeation buffer, then it becomes easy to exhibit the excessive-liquid permeation buffering effects. However, in the case where the gel strength is weakened by excessively enhancing the absorption capacity without load, there are disadvantage in that the absorption capacity of the water-absorbent resin under load might also be deteriorated, resulting in the deterioration of the absorption capacity in absorbent structures under load. Accordingly, before being mixed with the excessive-liquid permeation buffer, the water-absorbent resin needs to be well-balanced with regard to the absorption capacity without load and the absorption capacity under load, and is preferably a water-absorbent resin exhibiting an absorption capacity of not less than 37 g/g without load and an absorption capacity of not less than 32 g/g under load, and more preferably a water-absorbent resin exhibiting an absorption capacity of not less than 40 g/g without load and an absorption capacity of not less than 32 g/g under load, and still more preferably a water-absorbent resin exhibiting an absorption capacity of not less than 42 g/g without load and an absorption capacity of not less than 32 g/g under load.

In addition, high-molecular polycations are also usable as excessive-liquid permeation buffers which are in the form other than the fine particles. Specific examples thereof include polyethylenimine having a weight-average molecular weight of not lower than 2,000.

The above excessive-liquid permeation buffers may be used either alone respectively or in combinations with each other.

The average particle diameter of primary particles of the excessive-liquid permeation buffer can fitly be set according to uses, but is preferably not larger than 1/5, more preferably not larger than 1/10, still more preferably not larger than 1/20, of the average particle diameter of the water-absorbent resin so that the water-absorbing composition can favorably exhibit a high liquid permeation buffering index. In the case where the average particle diameter of the excessive-liquid permeation buffer is larger than 1/5 of the average particle diameter of the water-absorbent resin, there are disadvantages in that the affinity between the excessive-liquid permeation buffer and the aqueous liquid is so low that it takes a long time to exhibit excessive-liquid permeation buffering effects.

The mixing ratio between the water-absorbent resin and the excessive-liquid permeation buffer is not especially limited, but the ratio of the excessive-liquid permeation buffer is preferably in the range of 0.001~20 weight parts, more preferably 0.01~10 weight parts, still more preferably 0.02~5 weight parts, per 100 weight parts of the water-absorbent resin. In the case where the ratio of the excessive-liquid permeation buffer is lower than 0.001 weight parts per 100 weight parts of the water-absorbent resin, the below-mentioned liquid permeation buffering index cannot be improved. In addition, in the case where the ratio of the excessive-liquid permeation buffer is more than 20 weight parts per 100 weight parts of the water-absorbent resin, excessive-liquid permeation buffering effects are exhibited in absorbent structures having a resin concentration of 20~50 weight %, with the result that the water absorption properties of the absorbent structures are deteriorated.

Preferable examples of a mixing apparatus as used to mix the water-absorbent resin and the excessive-liquid permeation buffer together (this mixing apparatus is hereinafter referred to as "mixing apparatus b") include cylinder type mixers, screw type mixers, screw type extruders, turbilizers, Nauta mixers, V-character-shaped mixers, ribbon type mixers, twin-arm kneaders, fluidizing type mixers, rotary disk type mixers, roll mixers, and tumbling type mixers. The mixing speed may be either high or low.

Examples of the method for mixing the excessive-liquid permeation buffer with the water-absorbent resin include: a method involving dry blend; a method involving dry blend and then granulation with water; a method involving dry blend and then heat fusion; a method which involves mixing after dispersing the excessive-liquid permeation buffer into an aqueous solution; and a method which involves mixing in a state of an emulsion containing the above-exemplified hydrophilic organic solvent. Among them, the method involving dry blend and the method involving dry blend, and then adding and mixing water or an aqueous liquid including water and the above-exemplified hydrophilic organic solvent, and then granulation with water are preferable. In addition, the excessive-liquid permeation buffer may be dissolved or dispersed into the above-exemplified surface-crosslinking agent, thereby adding the excessive-liquid permeation buffer simultaneously with mixing the surface-crosslinking agent into the water-absorbent resin precursor.

The water-absorbing composition, obtained in the above way, has a liquid permeation buffering index of preferably not less than 0.4, more preferably not less than 0.5, still more preferably not less than 0.6, most preferably not less than 0.7. In the case where the liquid permeation buffering index of the water-absorbing composition is less than 0.4, the effect for the water-absorbing composition to prevent the aqueous liquid from diffusing (excessive-liquid permeation buffering effect) is not exhibited, therefore even if absorbent structure portions containing the water-absorbing composition in a high concentration are placed on the periphery, it is difficult for the absorbent structure portions to exhibit excessive-liquid permeation buffering effects, and liquid leakage from edge portions easily occurs in the use for sanitary materials such as diapers.

In addition, as to the water-absorbing composition according to the present invention, the absorption capacity of the water-absorbing composition in absorbent structures under load is preferably not less than 25 g/g, more preferably not less than 28 g/g, still more preferably not less than 30 g/g. In the case where the absorption capacity of the water-absorbing composition in absorbent structures under load is less than 25 g/g, there are disadvantages in that the wet back might increase in the use for diapers, with the result that babies' (wearers') buttocks might lack a dryness feeling or non-tacky feeling.

In addition, the water-absorbing composition, according to the present invention, exhibits an absorption capacity of preferably not less than 35 g/g, more preferably not less than 40 g/g, without load. In the case where the absorption capacity of the water-absorbing composition without load is less than 35 g/g, not only is the absorption capacity of the water-absorbing composition in absorbent structures under load low, but also a large quantity of water-absorbing composition is needed for obtaining a desired absorption capacity in absorbent articles, therefore there are disadvantages in that the concentration of the water-absorbing composition in the absorbent structures is so high that the diffusion of aqueous liquids is hindered also in portions where the diffusion of aqueous liquids is needed.

Furthermore, it is preferable that the water-absorbing composition according to the present invention has an average particle diameter in the range of 200~600 $\mu$m, and that the ratio of particles having particle diameters smaller than 106 $\mu$m in the water-absorbing composition is not more than 5 weight %, more preferably not more than 3 weight %, still more preferably not more than 1 weight %. In the case where the average particle diameter of the water-absorbing composition is larger than 600 $\mu$m, there are disadvantages in that the ratio of coarse particles is so high that the coarse particles give users an uncomfortable feeling when the water-absorbing composition is practically used for absorbent articles. In addition, in the case where the average particle diameter of the water-absorbing composition is smaller than 200 $\mu$m, there are disadvantages in that such a small average particle diameter involves the increase of the ratio of particles having particle diameters smaller than 106 $\mu$m. In addition, in the case where the ratio of particles having particle diameters smaller than 106 $\mu$m in the water-absorbing composition is more than 5 weight %, openings in absorbent structures are clogged with fines particles, therefore the absorption capacity of the water-absorbing composition in absorbent structures under load might be so low as to cause leakage. Particularly, in the case where the ratio of particles having particle diameters smaller than 106 $\mu$m is more than 5 weight %, powder dust occurs, so there are disadvantages in respect to working environment.

Figure 3:
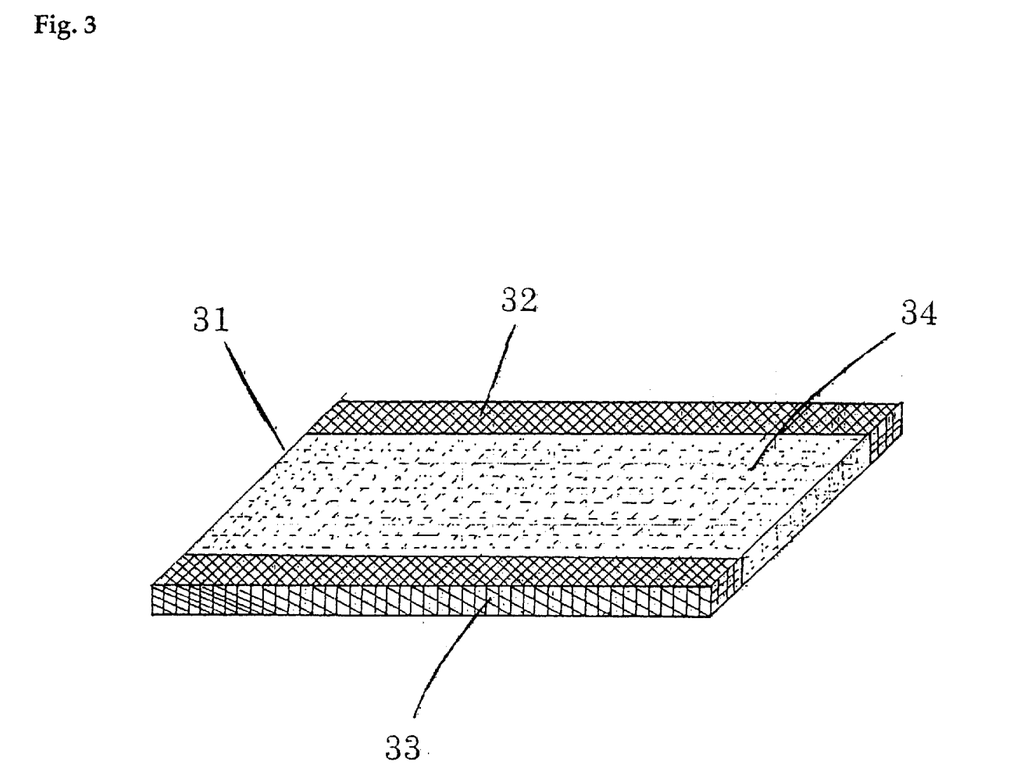
FIG. 3 is a schema of an absorbent structure as used for an absorbent article according to the present invention.

FIG. 3 is a schema showing an embodiment of the present invention. The absorbent structure 31 comprises hydrophilic pulp (hydrophilic fibers) and the water-absorbing composition according to the present invention. This absorbent structure is preferably an absorbent structure having side edge portions 32 and 33 and a central portion 34.

The side edge portions of the absorbent structure are outer peripheral portions having a certain width from edges of the absorbent structure. The side edge portions may be either all or part of the outer peripheral portions of the absorbent structure. In addition, the width of the side edge portions is preferably not more than 3 cm, more preferably not more than 2 cm, still more preferably not more than 1 cm.

The central portion of the absorbent structure is the portion other than the side edge portions of the absorbent structure.

The respective resin concentrations of the side edge portion and the central portion is not especially limited, but preferably there is a difference between the resin concentrations of the side edge portion and the central portion. When there is a difference between the resin concentrations of the side edge portion and the central portion, it is preferable that the resin concentration of the side edge portion is in the range of 51~98 weight %, and the resin concentration of the central portion is in the range of 5~50 weight %, and it is more preferable that the resin concentration of the side edge portion is in the range of 61~90 weight %, and the resin concentration of the central portion is in the range of 10~45 weight %, and it is still more preferable that the resin concentration of the side edge portion is in the range of 71~80 weight %, and the resin concentration of the central portion is in the range of 15~40 weight %.

Incidentally, if the above absorbent structure comprises a mixture of hydrophilic fibers and the water-absorbing composition according to the present invention as main components, then this absorbent structure may further comprise such as thermoplastic resins or binders, and is not especially limited.

In addition, the use of the absorbent structure is not especially limited, but the absorbent structure is preferably used for absorbent articles comprising such as a liquid-permeable sheet, a liquid-impermeable sheet, and a tape fastener. When the absorbent structure is used for absorbent articles, aqueous liquids (e.g. body fluids) as absorbed from the central portion diffuses into the side edge portions. The side edge portions contain the water-absorbing composition according to the present invention in such a high concentration that the diffusion of the aqueous liquids is inhibited to prevent the liquid leakage from the side edge portions.

If the absorbent article of the above constitution is used for disposable diapers, then the resultant disposable diapers involve so little wet back and liquid leakage as not to give wearers an uncomfortable feeling, because the water-absorbing composition according to the present invention has a liquid permeation buffering index of not less than 0.4 and exhibits an absorption capacity of not less than 25 g/g in absorbent structures under load, and further has an average particle diameter in the range of 200~600 μm, and further because the ratio of particles having particle diameters smaller than 106 μm in the water-absorbing composition is not more than 5 weight %.

Furthermore, it has been found that the absorbent article involving the use of the water-absorbing composition according to the present invention makes weak bonds between particles or between particle and fiber when absorbing aqueous liquids, and is therefore also excellent in the shape retainability.

Effects and Advantages of the Invention

The water-absorbing composition according to the present invention exhibits a high absorption capacity in absorbent articles, and further exhibits excessive-liquid permeation buffering effects greatly in high concentration portions where particles of the water-absorbing composition closely cohere. Accordingly, there are advantages in that: even if an aqueous liquid is injected in a large quantity at once into an absorbent article, the aqueous liquid can be prevented from leaking out from edge portions of the absorbent article due to too fast diffusion rate of the aqueous liquid in the absorbent article, with the result that a large quantity of aqueous liquid can be retained.

The absorbent article according to the present invention involves the use of the water-absorbing composition according to the present invention and therefore undergoes little liquid leakage from the periphery of the absorbent article in spite of extremely high water absorbency inside the absorbent article.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples.

EXAMPLE 1

A reaction solution was prepared by dissolving 5.91 g of polyethylene glycol diacrylate (as an internal-crosslinking agent) (average molar number of addition of ethylene oxide=8) into 5,500 g of a 35.5 weight % aqueous solution of sodium acrylate (hydrophilic unsaturated monomer) having a neutralization ratio of 75 mol %. Next, this solution was degassed under nitrogen gas atmosphere for 30 minutes (oxygen as dissolved in this solution was removed by introducing nitrogen gas into this solution for 30 minutes), and then the resultant solution was supplied into a reactor as prepared by lidding a jacketed stainless-steel-made twin-arm kneader of 10 liters in capacity having two sigma type blades. While maintaining the reaction solution at 30° C., the internal air of the system was replaced with nitrogen gas.

Next, while the reaction solution was stirred, a polymerization initiator comprising a combination of 2.67 g of sodium persulfate and 0.011 g of L-ascorbic acid was added, with the result that a polymerization reaction started about 1 minute after. Then, this polymerization reaction was carried out in the range of 20~80° C. and, 60 minutes after the initiation of the polymerization reaction, the polymerization reaction was finished to get out the resultant hydrogel polymer.

The resultant hydrogel polymer had a finely divided diameter of about 5 mm. This finely divided hydrogel polymer was spread onto a 50-mesh metal gauze (mesh opening size=300 μm) and then dried at 170° C. with hot air for 65 minutes. Then, the resultant dried product was pulverized with a vibration mill and then classified with metal gauzes of 500 μm and 425 μm in mesh opening size, thus obtaining a water-absorbent resin precursor having particle diameters of 500 μm~425 μm.

An amount of 100 weight parts of the resultant water-absorbent resin precursor was mixed with an aqueous surface-crosslinking agent solution comprising 0.03 weight parts of ethylene glycol diglycidyl ether, 1 weight part of propylene glycol, 3 weight parts of water, and 1 weight part of isopropyl alcohol. The resultant mixture was heated at 205° C. for 40 minutes, thus obtaining a water-absorbent resin.

An amount of 100 weight parts of the resultant water-absorbent resin was dry-blended with 2.5 weight parts of a crosslinked acrylic acid polymer (trade name: Carbopole 934 P; produced by B.F. Goodrich Company; 1 weight % aqueous solution viscosity=40,000 cP (1 cP=$10^{-3}$ Pa·s) (1 weight % aqueous solution viscosity=40 Pa·s)) as an excessive-liquid permeation buffer, thus obtaining a water-absorbing composition according to the present invention.

The absorption capacity without load and the liquid permeation buffering index of the resultant water-absorbing composition were 36 g/g and 0.5 respectively, and the absorption capacity of the resultant water-absorbing composition in absorbent structures under load was 31 g/g. In addition, the particle diameters of the resultant water-absorbing composition were almost unchanged from those of the water-absorbent resin precursor and were therefore in the range of 500 μm~425 μm.

EXAMPLE 2

A water-absorbing composition was obtained in the same way as of Example 1 except that the amount of the crosslinked acrylic acid polymer (trade name: Carbopole 934 P; produced by B.F. Goodrich Company; 1 weight % aqueous solution viscosity=40,000 cP (1 weight % aqueous solution viscosity=40 Pa·s)) as added was changed to 5 weight parts. The absorption capacity without load and the liquid permeation buffering index of the resultant water-absorbing composition were 36 g/g and 0.8 respectively, and the absorption capacity of the resultant water-absorbing composition in absorbent structures under load was 30 g/g. In addition, the particle diameters of the resultant water-absorbing composition were in the range of 600 μm~425 μm, and the ratio of particles having particle diameters smaller than 106 μm in the water-absorbing composition was less than 1 weight %.

EXAMPLE 3

A water-absorbing composition was obtained in the same way as of Example 1 except that the sort and the amount of the excessive-liquid permeation buffer as added were changed to a crosslinked acrylic acid polymer (trade name: Junron PW-150; produced by Nippon Pure Chemical Industries, Ltd.; 1 weight % aqueous solution viscosity=95,000 cP (1 weight % aqueous solution viscosity=95 Pa·s)) and 2 weight parts respectively. The absorption capacity without load and the liquid permeation buffering index of the resultant water-absorbing composition were 37 g/g and 0.5 respectively, and the absorption capacity of the resultant water-absorbing composition in absorbent structures under load was 32 g/g. In addition, the particle diameters of the resultant water-absorbing composition were almost unchanged from those of the water-absorbent resin precursor and were therefore in the range of 500 μm~425 μm.

EXAMPLE 4

A water-absorbing composition was obtained in the same way as of Example 3 except that the amount of the crosslinked acrylic acid polymer (trade name: Junron PW-150; produced by Nippon Pure Chemical Industries, Ltd.; 1 weight % aqueous solution viscosity=95,000 cP (1 weight % aqueous solution viscosity=95 Pa·s)), as added as the excessive-liquid permeation buffer, were changed to 5 weight parts. The absorption capacity without load and the liquid permeation buffering index of the resultant water-absorbing composition were 36 g/g and 1 respectively, and the absorption capacity of the resultant water-absorbing composition in absorbent structures under load was 30 g/g. In addition, the particle diameters of the resultant water-absorbing composition were in the range of 600 μm~425 μm, and the ratio of particles having particle diameters smaller than 106 μm in the water-absorbing composition was less than 1 weight %.

EXAMPLE 5

An amount of 5 weight parts of a crosslinked acrylic acid polymer (trade name: Carbopole 934 P; produced by B.F. Goodrich Company; 1 weight % aqueous solution viscosity= 40,000 cP (1 weight % aqueous solution viscosity=40 Pa·s)) (as an excessive-liquid permeation buffer) was added and mixed into 100 weight parts of the water-absorbent resin as obtained in Example 1. Then, the resultant mixture was mixed with an aqueous solution comprising 3 weight parts of water and 3 weight parts of isopropyl alcohol and thereby granulated with water. Furthermore, the resultant mixture was cured at 80° C. for 30 minutes, and then allowed to pass through a screen of 600 μm in mesh opening size, thus obtaining a water-absorbing composition according to the present invention. The absorption capacity without load and the liquid permeation buffering index of the resultant water-absorbing composition were 38 g/g and 0.5 respectively, and the absorption capacity of the resultant water-absorbing composition in absorbent structures under load was 31 g/g. In addition, the particle diameters of the resultant water-absorbing composition were in the range of 600 μm~425 μm.

COMPARATIVE EXAMPLE 1

The water-absorbent resin as obtained in Example 1 was taken as a comparative water-absorbing agent (comparative water-absorbing agent (1)). The performances of this comparative water-absorbing agent were measured by the aforementioned methods. As a result, the absorption capacity without load and the liquid permeation buffering index of the water-absorbing agent (comparative water-absorbing agent (1)) were 37 g/g and 0.3 respectively, and the absorption capacity of the water-absorbing agent (comparative water-absorbing agent (1)) in absorbent structures under load was 32 g/g.

EXAMPLE 6

A reaction solution was prepared by dissolving 2.22 g of polyethylene glycol diacrylate (as an internal-crosslinking agent) (average molar number of addition of ethylene oxide=8) into 5,500 g of a 37 weight % aqueous solution of sodium acrylate (hydrophilic unsaturated monomer) having a neutralization ratio of 75 mol %. Next, this solution was degassed under nitrogen gas atmosphere for 30 minutes (oxygen as dissolved in this solution was removed by introducing nitrogen gas into this solution for 30 minutes), and then the resultant solution was supplied into a reactor as prepared by lidding a jacketed stainless-steel-made twin-arm kneader of 10 liters in capacity having two sigma type blades. While maintaining the reaction solution at 25° C., the internal air of the system was replaced with nitrogen gas.

Next, while the reaction solution was stirred, a polymerization initiator comprising a combination of 2.4 g of sodium persulfate and 0.12 g of L-ascorbic acid was added, with the result that a polymerization reaction started about 1 minute after. Then, this polymerization reaction was carried out in the range of 25~95° C. and, 40 minutes after the initiation of the polymerization reaction, the polymerization reaction was finished to get out the resultant hydrogel polymer.

The resultant hydrogel polymer had a finely divided diameter of about 5 mm. This finely divided hydrogel polymer was spread onto a 50-mesh metal gauze (mesh opening size=300 μm) and then dried at 170° C. with hot air for 70 minutes. Then, the resultant dried product was pulverized with a vibration mill and then classified, thus obtaining a water-absorbent resin precursor (a) of the irregular pulverized shape.

An amount of 100 weight parts of the resultant water-absorbent resin precursor (a) was mixed with an aqueous surface-crosslinking agent solution comprising 0.8 weight parts of propylene glycol, 0.03 weight parts of ethylene glycol diglycidyl ether, 2.5 weight parts of water, and 0.8 weight parts of ethyl alcohol. The resultant mixture was heated at 195° C. for 45 minutes, thus obtaining a water-absorbent resin (a), of which the absorption capacity without load was 46 g/g, the absorption capacity under load was 36 g/g, the average particle diameter was 350 μm, and the ratio of particles having particle diameters smaller than 106 μm was 1 weight %.

Next, 0.3 g of fine particulate hydrophilic silicon dioxide (trade name: Aerosil 200 (average particle diameter of primary particles=about 12 nm); produced by Nippon Aerosil Co., Ltd.) (as an excessive-liquid permeation buffer) was added and mixed (dry-blended) into 100 g of the resultant water-absorbent resin (a), thus obtaining a water-absorbing composition (6) according to the present invention. The particle diameters of the resultant water-absorbing composition (6) were almost unchanged from those of the water-absorbent resin (a), therefore the average particle diameter of the water-absorbing composition was 350 μm, and the ratio of particles having particle diameters smaller than 106 μm in the water-absorbing composition was 1 weight %.

The performances of the above water-absorbing composition were measured by the aforementioned methods. Results thereof are shown in Table 1.

EXAMPLE 7

A water-absorbing composition (7) according to the present invention was obtained by adding and mixing (dry-blending) 0.1 g of fine particulate hydrophobic silicon dioxide (trade name: Aerosil R972 (average particle diameter of primary particles=about 16 nm); produced by Nippon Aerosil Co., Ltd.) (as an excessive-liquid permeation buffer) into 100 g of the water-absorbent resin (a) as obtained in Example 6 above. The particle diameters of the resultant water-absorbing composition (7) were almost unchanged from those of the water-absorbent resin (a), therefore the average particle diameter of the water-absorbing composition was 350 μm, and the ratio of particles having particle diameters smaller than 106 μm in the water-absorbing composition was 1 weight %.

The performances of the above water-absorbing composition were measured by the aforementioned methods. Results thereof are shown in Table 1.

EXAMPLE 8

A water-absorbing composition (8) according to the present invention was obtained by adding and mixing (dry-blending) 0.2 g of fine particulate cationic hydrophobic silicon dioxide (trade name: Aerosil RA200HS; produced by Nippon Aerosil Co., Ltd.) (as an excessive-liquid permeation buffer) into 100 g of the water-absorbent resin (a) as obtained in Example 6 above. The particle diameters of the resultant water-absorbing composition (8) were almost unchanged from those of the water-absorbent resin (a), therefore the average particle diameter of the water-absorbing composition was 350 μm, and the ratio of particles having particle diameters smaller than 106 μm in the water-absorbing composition was 1 weight %.

The performances of the above water-absorbing composition were measured by the aforementioned methods. Results thereof are shown in Table 1.

EXAMPLE 9

A water-absorbing composition (9) according to the present invention was obtained by adding and mixing (dry-blending) 1.5 g of polyethylenimine (weight-average molecular weight=10,000) (trade name: Epomin SP-200; produced by Nippon Shokubai Co., Ltd.) (as an excessive-liquid permeation buffer) into 100 g of the water-absorbent resin (a) as obtained in Example 6 above. As to the resultant water-absorbing composition (9), the average particle diameter was 380 μm, and the ratio of particles having particle diameters smaller than 106 μm was 1 weight %.

The performances of the above water-absorbing composition were measured by the aforementioned methods. Results thereof are shown in Table 1.

EXAMPLE 10

A reaction solution was prepared by dissolving 4.46 g of polyethylene glycol diacrylate (as an internal-crosslinking agent) (average molar number of addition of ethylene oxide=8) into 5,500 g of a 33 weight % aqueous solution of sodium acrylate (hydrophilic unsaturated monomer) having a neutralization ratio of 75 mol %. Next, this solution was degassed under nitrogen gas atmosphere for 30 minutes (oxygen as dissolved in this solution was removed by introducing nitrogen gas into this solution for 30 minutes), and then the resultant solution was supplied into a reactor as prepared by lidding a jacketed stainless-steel-made twin-arm kneader of 10 liters in capacity having two sigma type blades. While maintaining the reaction solution at 25° C., the internal air of the system was replaced with nitrogen gas.

Next, while the reaction solution was stirred, a polymerization initiator comprising a combination of 2.4 g of ammonium persulfate and 0.12 g of L-ascorbic acid was added, with the result that a polymerization reaction started about 1 minute after. Then, this polymerization reaction was carried out in the range of 25~90° C. and, 40 minutes after the initiation of the polymerization reaction, the polymerization reaction was finished to get out the resultant hydrogel polymer.

The resultant hydrogel polymer had a finely divided diameter of about 5 mm. This finely divided hydrogel polymer was spread onto a 50-mesh metal gauze (mesh opening size=300 μm) and then dried at 170° C. with hot air for 70 minutes. Then, the resultant dried product was pulverized with a vibration mill and then classified, thus obtaining a water-absorbent resin precursor (b) of the irregular pulverized shape.

An amount of 100 weight parts of the resultant water-absorbent resin precursor (b) was mixed with an aqueous surface-crosslinking agent solution comprising 0.7 weight parts of propylene glycol, 0.02 weight parts of ethylene glycol diglycidyl ether, 2 weight parts of water, and 0.7 weight parts of ethyl alcohol. The resultant mixture was heated at 185° C. for 40 minutes, thus obtaining a water-absorbent resin (b), of which the absorption capacity without load was 43 g/g, the absorption capacity under load was 32 g/g, the average particle diameter was 430 μm, and the ratio of particles having particle diameters smaller than 106 μm was 3 weight %.

Next, 0.3 g of fine particulate hydrophilic silicon dioxide (trade name: Aerosil 200 (average particle diameter of primary particles=about 12 nm); produced by Nippon Aerosil Co., Ltd.) (as an excessive-liquid permeation buffer) was added and mixed (dry-blended) into 100 g of the resultant water-absorbent resin (b), thus obtaining a water-absorbing composition (10) according to the present invention. The particle diameters of the resultant water-absorbing composition (10) were almost unchanged from those of the water-absorbent resin (b), therefore the average particle diameter of the water-absorbing composition was 430 μm, and the ratio of particles having particle diameters smaller than 106 μm in the water-absorbing composition was 3 weight %.

The performances of the above water-absorbing composition were measured by the aforementioned methods. Results thereof are shown in Table 1.

COMPARATIVE EXAMPLE 2

A reaction solution was prepared by dissolving 2.72 g of trimethylolpropane triacrylate (as an internal-crosslinking agent) into 4,400 g of a 37 weight % aqueous solution of sodium acrylate (hydrophilic unsaturated monomer) having a neutralization ratio of 75 mol %. Next, this solution was degassed under nitrogen gas atmosphere for 30 minutes (oxygen as dissolved in this solution was removed by introducing nitrogen gas into this solution for 30 minutes), and then the resultant solution was supplied into the same reactor as that used in Example 6. While maintaining the reaction solution at 30° C., the internal air of the system was replaced with nitrogen gas.

Next, while the reaction solution was stirred, a polymerization initiator comprising a combination of 1.1 g of sodium persulfate and 1.1 g of sodium sulfite was added, with the result that a polymerization reaction started about 1 minute after. Then, this polymerization reaction was carried out in the range of 30~80° C. and, 40 minutes after the initiation of the polymerization reaction, the polymerization reaction was finished to get out the resultant hydrogel polymer.

The resultant hydrogel polymer had a finely divided diameter of about 5 mm. This finely divided hydrogel polymer was spread onto a 50-mesh metal gauze (mesh opening size=300 μm) and then dried at 150° C. with hot air for 120 minutes. Then, the resultant dried product was pulverized with a hammer mill and then classified, thus obtaining a water-absorbent resin precursor (c) of the irregular pulverized shape.

An amount of 100 weight parts of the resultant water-absorbent resin precursor (c) was mixed with an aqueous surface-crosslinking agent solution comprising 1 weight part of propylene glycol, 0.05 weight parts of ethylene glycol diglycidyl ether, 3 weight parts of water, and 0.75 weight parts of isopropyl alcohol. The resultant mixture was heated at 175° C. for 40 minutes, thus obtaining a water-absorbent resin (c), of which the absorption capacity without load was 40 g/g, the absorption capacity under load was 32 g/g, the average particle diameter was 350 μm, and the ratio of particles having particle diameters smaller than 106 μm was 8 weight %.

Next, 1 g of fine particulate hydrophilic silicon dioxide (trade name: Aerosil 200 (average particle diameter of primary particles=about 12 nm); produced by Nippon Aerosil Co., Ltd.) (as an excessive-liquid permeation buffer) was added and mixed (dry-blended) into 100 g of the resultant water-absorbent resin (c), thus obtaining a comparative water-absorbing composition (2). The particle diameters of the resultant comparative water-absorbing composition (2) were almost unchanged from those of the water-absorbent resin (c), therefore the average particle diameter of the water-absorbing composition was 350 μm, and the ratio of particles having particle diameters smaller than 106 μm in the water-absorbing composition was 8 weight %.

The performances of the above water-absorbing composition were measured by the aforementioned methods. Results thereof are shown in Table 1.

TABLE 1

| | Absorption capacity (g/g) without load | Liquid permeation buffering index | Absorption capacity (g/g) in absorbent structures under load | Average particle diameter (μm) | Ratio (wt %) of particles having particle diameters smaller than 106 μm |
|---|---|---|---|---|---|
| Example 1 | 36 | 0.5 | 31 | 463 | 0 |
| Example 2 | 36 | 0.8 | 30 | 513 | <1 |
| Example 3 | 37 | 0.5 | 32 | 463 | 0 |
| Example 4 | 38 | 1 | 30 | 513 | <1 |
| Example 5 | 38 | 0.5 | 31 | 513 | 0 |
| Example 6 | 46 | 0.59 | 35.7 | 350 | 1 |
| Example 7 | 46 | 0.61 | 35.2 | 350 | 1 |
| Example 8 | 45 | 0.63 | 35.0 | 350 | 1 |
| Example 9 | 43 | 0.67 | 32.0 | 380 | 1 |
| Example 10 | 43 | 0.83 | 31.0 | 430 | 3 |
| Comparative Example 1 | 37 | 0.3 | 32 | 463 | 0 |
| Comparative Example 2 | 37 | 0.59 | 28.0 | 350 | 8 |

EXAMPLE 11

An absorbent structure was produced from the water-absorbing composition, as obtained in Example 1, and wood-pulverized pulp as usually used for sanitary materials such as disposable diapers. This absorbent structure was of the size of 120 mm×400 mm comprising an outer peripheral portion of the width of 1 cm and a central portion of the size of 100 mm×380 mm, and had water-absorbing composition concentrations of 75 weight % and 50 weight % in the outer peripheral portion and in the central portion respectively. The production process for this absorbent structure is specified as follows. The outer peripheral portion of the absorbent structure was produced by mixing 75 weight parts of water-absorbing composition and 25 weight parts of wood-pulverized pulp (as hydrophilic fibers) together in a dry manner with a mixer, and then shaping the resultant mixture into an outer peripheral portion of a web, which had a basis weight of about 0.094 g/cm² as the outer peripheral portion. In addition, the central portion of the absorbent structure was produced by mixing 50 weight parts of water-absorbing composition and 50 weight parts of wood-pulverized pulp (as hydrophilic fibers) together in a dry manner with a mixer, and then shaping the resultant mixture into a central portion of the above web, which had a basis weight of about 0.047 g/cm² as the central portion. The resultant web was pressed under a pressure of 2 kg/cm² (=about 196 kPa) for 1 minute, thus obtaining the absorbent structure.

Next, a back sheet (liquid-impermeable sheet) of a liquid-impermeable polypropylene with a so-called leg gather, the above absorbent structure, and a top sheet (liquid-permeable sheet) of a liquid-permeable polypropylene were attached to each other in this order with double coated tapes, and two so-called tape fasteners were then provided to the resultant attached product, thus obtaining an absorbent article (i.e. disposable diaper). The weight of this absorbent article was 51 g.

This absorbent article was fitted up to a so-called Kewpie (trademark) doll (stature: 55 cm, weight: 5 kg), and this doll was laid on its face. Thereafter, a tube was inserted between the absorbent article and the doll to inject 50 ml of physiological saline solution every 20 minutes into a position corresponding to where urine was discharged from a human body. Then, this injection operation was ended when the injected physiological saline solution began leaking out without being absorbed by the absorbent article, and the number of times of the injection was recorded.

As a result, as shown in Table 2, the number of times of the injection was 6 (total injection quantity=300 ml).

EXAMPLE 12

An absorbent article was obtained in the same way as of Example 11 except that the water-absorbing composition, as obtained in Example 1, was replaced with the water-absorbing composition (6) as obtained in Example 6. The weight of this absorbent article was 51 g.

This absorbent article was measured in the same way as of Example 11 to record the number of times of the injection. As a result, as shown in Table 2, the number of times of the injection was 6 (total injection quantity=300 ml).

COMPARATIVE EXAMPLE 3

A comparative absorbent article was obtained in the same way as of Example 11 except that the water-absorbing composition, as obtained in Example 1, was replaced with the comparative water-absorbing agent (comparative water-absorbing agent (1)) as obtained in Comparative Example 1. The weight of this comparative absorbent article was 51 g.

This comparative absorbent article was measured in the same way as of Example 11 to record the number of times of the injection. As a result, as shown in Table 2, the number of times of the injection was 5 (total injection quantity=250 ml).

COMPARATIVE EXAMPLE 4

A comparative absorbent article was obtained in the same way as of Example 11 except that the water-absorbing composition, as obtained in Example 1, was replaced with the comparative water-absorbing composition (2) as obtained in Comparative Example 2. The weight of this comparative absorbent article was 51 g.

This comparative absorbent article was measured in the same way as of Example 11 to record the number of times of the injection. As a result, as shown in Table 2, the number of times of the injection was 5 (total injection quantity=250 ml).

TABLE 2

| | Number of times of injection | Total injection quantity (ml) |
| --- | --- | --- |
| Example 11 | 6 | 300 |
| Example 12 | 6 | 300 |
| Comparative Example 3 | 5 | 250 |
| Comparative Example 4 | 5 | 250 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-absorbing composition, which comprises a mixture of a water-absorbent resin and an excessive-liquid permeation buffer, wherein the water-absorbent resin is a product obtained by a process including the step of further crosslinking the surface vicinity of a crosslinked polymer having an average particle diameter in the range of 200–600 $\mu$m, wherein the ratio of particles having particle diameters smaller than 106 $\mu$m in the crosslinked polymer is not more than 5 weight %, with the water-absorbing composition being characterized by having a liquid permeation buffering index of not less than 0.4 and exhibiting an absorption capacity of not less than 25 g/g in absorbent structures under load, and further having an average particle diameter in the range of 200–600 $\mu$m, wherein the ratio of particles having particle diameters smaller than 106 $\mu$m in the water-absorbing composition is not more than 5 weight %, wherein:

said liquid permeation buffering index is calculated by the following formula:

Liquid permeation buffering index=10/{(weight W$_1$ (g))/(weight (g) of water-absorbing composition)} wherein W$_1$ is the weight in grams of a physiological saline solution absorbed by said water-absorbing composition over a period of 60 minutes under a load of 20 g/cm² (=about 1.9 kPa); and the conditions for measuring said absorption capacity in absorbent structures under load are that: (i) the load is 20 g/cm² (=about 1.9 kPa); (ii) the liquid being absorbed is physiological saline solution; and (iii) the absorption quantity is measured over a period of 60 minutes.

2. A water-absorbing composition according to claim 1, which exhibits an absorption capacity of not less than 35 g/g without load.

3. A water-absorbing composition according to claim 1, which has a liquid permeation buffering index of not less than 0.5.

4. A water-absorbing composition according to claim 1, which exhibits an absorption capacity of not less than 30 g/g in absorbent structures under load.

5. A water-absorbing composition according to claim 1, wherein the water-absorbent resin exhibits an absorption capacity of not less than 37 g/g without load and an absorption capacity of not less than 32 g/g under load.

6. A water-absorbing composition according to claim 1, wherein the ratio of the excessive-liquid permeation buffer is in the range of 0.001 to 20 weight parts per 100 weight parts of the water-absorbent resin.

7. A water-absorbing composition according to claim 1, wherein the excessive-liquid permeation buffer is in the form of particles having an average particle diameter of not larger than 1/5 of that of the water-absorbent resin.

8. A water-absorbing composition according to claim 2, which has a liquid permeation buffering index of not less than 0.5.

9. A water-absorbing composition according to claim 2, which exhibits an absorption capacity of not less than 30 g/g in absorbent structures under load.

10. A water-absorbing composition, which comprises a mixture of a water-absorbent resin and an excessive-liquid permeation buffer, wherein the water-absorbent resin is a product obtained by a process including the step of further crosslinking the surface vicinity of a crosslinked polymer having an average particle diameter in the range of 200–600 $\mu$m, wherein the ratio of particles having particle diameters smaller than 106 $\mu$m in the crosslinked polymer is not more than 5 weight %, with the water-absorbing composition being characterized by having a liquid permeation buffering index of not less than 0.5 and exhibiting an absorption capacity of not less than 30 g/g in absorbent structures under load and an absorption capacity of not less than 40 g/g without load, and further having an average particle diameter in the range of 200–600 $\mu$m, wherein the ratio of particles having particle diameters smaller than 106 $\mu$m in the water-absorbing composition is not more than 5 weight %, wherein said liquid permeation buffering index is calculated by the following formula:

Liquid permeation buffering index=10/{(weight $W_1$ (g))/(weight (g) of water-absorbing composition)} wherein $W_1$ is the weight in grams of a physiological saline solution absorbed by said water-absorbing composition over a period of 60 minutes under a load of 20 g/cm$^2$ (=about 1.9 kPa); and the conditions for measuring said absorption capacity in absorbent structures under load are that: (i) the load is 20 g/cm$^2$ (=about 1.9 kPa); (ii) the liquid being absorbed is physiological saline solution; and (iii) the absorption quantity is measured over a period of 60 minutes.

11. A water-absorbing composition according to claim 10, which has a liquid permeation buffering index of not less than 0.6.

12. A water-absorbing composition according to claim 11, which has a liquid permeation buffering index of not less than 0.7.

13. An absorbent article, which comprises the water-absorbing composition as recited in claim 1.

14. The composition of claim 1, wherein said composition comprises particles of said excessive-liquid permeation buffer having a particle size to enable said particles of said composition to cohere sufficiently to prevent aqueous liquids from flowing between said particles.

15. The composition of claim 1, wherein said composition is prepared by dry blending said water-absorbent resin with said excessive-liquid permeation buffer to form a dry blend of said water absorbing composition.

16. The composition of claim 15, wherein said composition is prepared by granulating said dry blend with water.

17. The composition of claim 15, wherein said composition is prepared by fusing said dry blend by applying heat to said dry blend.

18. The composition of claim 10, wherein said composition comprises particles of said water absorbent resin and particles of said excessive-liquid permeation buffer to enable particles of said water absorbing composition to-cohere to prevent aqueous liquids from flowing between said particles.

19. The composition of claim 10, wherein said composition is prepared by dry blending said water-absorbent resin with said excessive-liquid permeation buffer to form a dry blend of said water absorbing composition.

20. The composition of claim 19, wherein said composition is prepared by granulating said dry blend with water.

21. The composition of claim 19, wherein said composition is prepared by fusing said dry blend by applying heat to said dry blend.

* * * * *